United States Patent [19]

Terahara et al.

[11] 4,447,626
[45] May 8, 1984

[54] ML-236B DERIVATIVES

[75] Inventors: Akira Terahara; Minoru Tanaka, both of Tokyo, Japan

[73] Assignee: Sankyo Company Limited, Tokyo, Japan

[21] Appl. No.: 395,968

[22] Filed: Jul. 7, 1982

[30] Foreign Application Priority Data

Jul. 21, 1981 [JP] Japan .................. 56-114038

[51] Int. Cl.³ .......................................... C07D 309/30
[52] U.S. Cl. .................................. 549/292; 560/119; 424/279
[58] Field of Search ........................................ 549/292

[56] References Cited

U.S. PATENT DOCUMENTS 3,983,140  9/1976  Endo et al. .................. 549/292
4,346,227  8/1982  Terahara et al. ............ 549/292

Primary Examiner—Norma S. Milestone
Attorney, Agent, or Firm—Frishauf, Holtz, Goodman & Woodward

[57] ABSTRACT

A compound of formula (I):

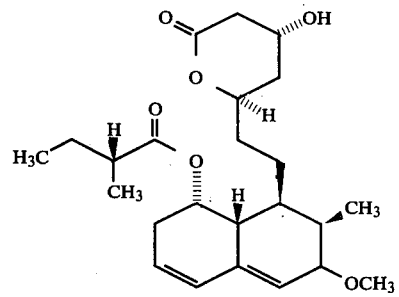

(called 6-methoxy-IsoML-236B lactone) and its corresponding free hydroxy-carboxylic acid and salts and esters of said acid may be prepared by the enzymatic alkoxylation of an ML-236B compound, preferably using a microorganism of the genus *Syncephalastrum*, *Absidia* or *Cunninghamella*, e.g. *Absidia coerulea*, or a cell-free enzyme-containing extract from said microorganism. If desired, the lactone or carboxylic acid may be converted by conventional salification or esterification techniques to the desired salt or ester. These compounds have the ability to inhibit the biosynthesis of cholesterol and are thus of value in the treatment of hypercholesteraemia, for which purpose they may be formulated as compositions in admixture with conventional pharmaceutical carriers or diluents.

1 Claim, No Drawings

ML-236B DERIVATIVES

BACKGROUND TO THE DISCLOSURE

The present invention relates to a series of new derivatives of the known compound ML-236B, to processes for their preparation and to pharmaceutical compositions containing them.

ML-236B is disclosed in U.S. Pat. No. 3,983,140 and the term "ML-236B" is used to refer to two compounds, a lactone, termed "ML-236B lactone", which has the structural formula:

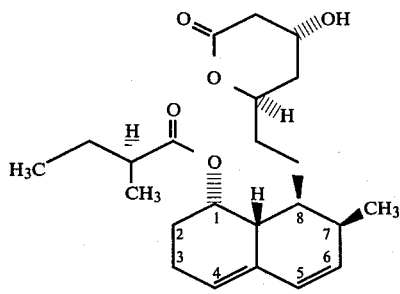

and the corresponding free hydroxy-carboxylic acid, termed "ML-236B carboxylic acid", which has the structural formula:

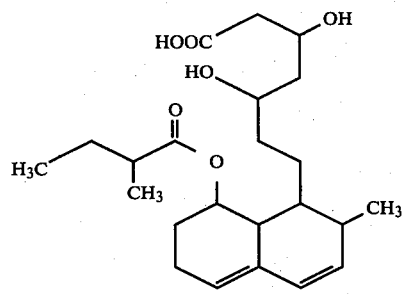

These ML-236B compounds have been isolated and purified from the metabolic products of microorganisms of the genus Penicillium, especially *Penicillium citrinum*, a species of blue mould. They have been shown to inhibit the biosynthesis of cholesterol by enzymes or cultured cells separated from experimental animals by competing with the rate-limiting enzyme active in the biosynthesis of cholesterol, that is to say 3-hydroxy-3-methylglutaryl-coenzyme A reductase, and, as a result, significantly reduce serum cholesterol levels in animals [Journal of Antibiotics, 29, 1346 (1976)].

A number of compounds structurally related to ML-236B have also been discovered and some have been found to share this ability to inhibit the biosynthesis of cholesterol. Of the ML-236B derivatives which have been discovered, the most relevant form the subject of copending U.S. patent application Ser. No. 270,846, filed 5th June 1981 which issued as U.S. Pat. No. 4,346,227. In the lactone form, these compounds may be represented by the structural formula:

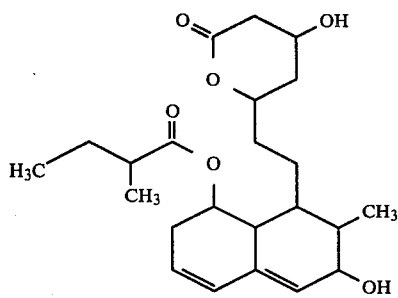

and have been named IsoM-4 lactone or IsoM-4' lactone, depending upon the particular configuration of the various asymmetric carbon atoms present in the molecule. The corresponding IsoM-4 carboxylic acid and IsoM-4' carboxylic acid are also disclosed and these compounds were all found to have the ability to inhibit the biosynthesis of cholesterol.

The IsoM-4 and IsoM-4' compounds and their alkali metal salts may be prepared by the enzymatic hydroxylation of ML-236B or of a derivative thereof and other salts and the esters may, of course, then be prepared by conventional salification or esterification procedures starting with the resulting hydroxylation product. The enzymatic hydroxylation is preferably effected using a suitable microorganism or an enzyme-containing extract of such a microorganism, although it may also be effected as part of the mammalian metabolism of ML-236B or by using the liver or an enzyme-containing extract from the liver of such an animal. Preferred microorganisms for use in this process include those of the genera Absidia, Cunninghamella, Syncephalastrum, We have now surprisingly discovered that the treatment of ML-236B lactone or ML-236B carboxylic acid or a salt or alkyl ester thereof with certain of these microorganisms or with enzyme-containing extracts therefrom can also produce other distinct, but related, compounds which likewise have the ability to inhibit the biosynthesis of cholesterol.

Moreover, the new compounds of the invention are metabolized with much greater difficulty after administration than is ML-236B. The compounds of the invention are thus less readily deactivated and hence have more persistent activity, with attendant advantages well recognized in the art.

BRIEF SUMMARY OF INVENTION

The compounds of the present invention are the lactone of formula (I):

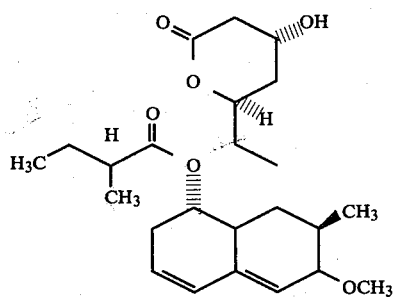

as well as its corresponding free hydroxy-carboxylic acid, which may be represented by the structural formula (II):

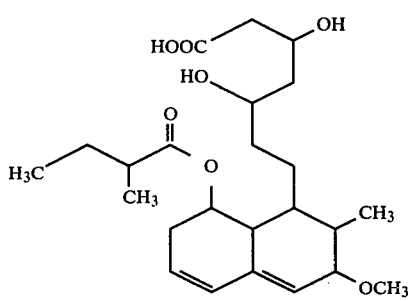

and pharmaceutically acceptable salts and esters of said acid.

The compound of formula (I) is referred to as 6-methoxy-IsoML-236B lactone and the compound of formula (II) is referred to as 6-methoxy-IsoML-236B carboxylic acid, the salts and esters being named accordingly.

The compounds of the invention may be prepared by the enzymatic alkoxylation of ML-236B lactone, ML-236B carboxylic acid or a salt or ester of said carboxylic acid.

The invention also provides a pharmaceutical composition for the reduction of blood cholesterol levels, comprising an active ingredient in admixture with a pharmaceutically acceptable carrier or diluent, wherein the active ingredient is at least one compound selected from the compound of formula (I), the corresponding free hydroxy-carboxylic acid and salts and esters of said acids.

DETAILED DESCRIPTION OF INVENTION

The salts of 6-methoxy-IsoML-236B carboxylic acid may be metal salts, ammonium salts or salts with organic amines or amino acids.

Metal salts of 6-methoxy-IsoML-236B carboxylic acid may be represented by formula (III):

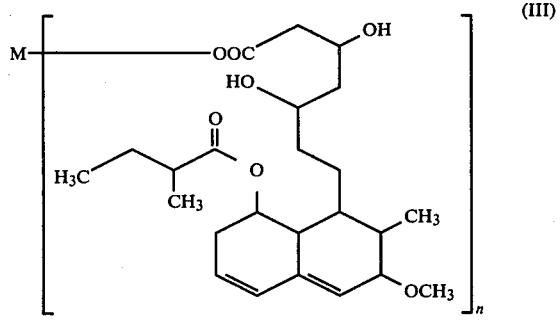

(in which M represents a metal atom and n represents the valency of the metal atom). Examples of metals which may be represented by M in these salts include: alkali metals, such as sodium or potassium; alkaline earth metals, such as calcium; and other metals, such as magnesium, aluminium, iron, zinc, cobalt or nickel. Of these metals, the alkali metals, alkaline earth metals and aluminium are preferred, sodium and potassium being most preferred.

The ammonium, organic amine and amino acid salts of 6-methoxy-IsoML-236B carboxylic acid may be represented by formula (IV):

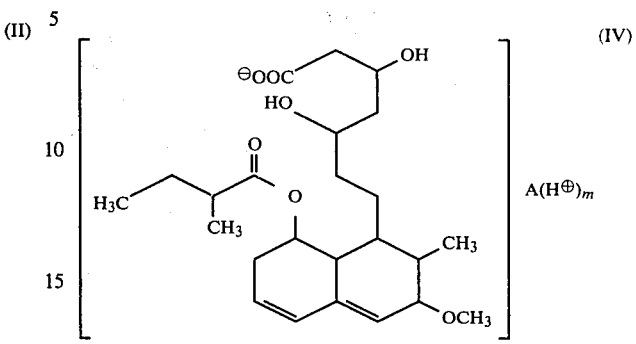

(in which A represents ammonia, an amino acid or an organic amine, and m is an integer). The integer represented by m is preferably 1, that is to say the amine or amino acid represented by A is preferably monoacidic.

Examples of amino acids which may be represented by A in the above formula (IV) include such basic amino acids as arginine, lysine, histidine, 2,4-diaminobutyric acid and ornithine.

When A represents an organic amine, it is preferably a monoamine and may be an aliphatic, aromatic, alicyclic, heterocyclic or carbohydrate monoamine. Examples include: primary alkylamines, such as octylamine, t-octylamine or 2-ethylhexylamine; primary, secondary and tertiary $C_7$ or $C_8$ aralkylamines, such as benzylamine, α-methylbenzylamine, phenethylamine, dibenzylamine, N-methylbenzylamine, N,N-dimethylbenzylamine, N,N-diethylbenzylamine, N-ethyl-N-methylbenzylamine or tribenzylamine; primary, secondary or tertiary $C_5$–$C_7$ saturated alicyclic amines, such as cyclopentylamine, cyclohexylamine, cycloheptylamine, N-methylcyclopentylamine, N-ethylcyclohexylamine, N-ethylcycloheptylamine, dicyclohexylamine, N,N-dimethylcyclopentylamine, N,N-dimethylcyclohexylamine or N,N-diethylcycloheptylamine; 5 or 6 membered heterocyclic amines having a single nitrogen atom as the hetero atom, such as pyrrolidine, N-methylpyrrolidine, piperidine or N-methylpiperidine; morpholine; $C_1$–$C_3$ alkyl esters of aliphatic or aromatic amino acids, such as leucine methyl ester, diethyl glutamate, phenylglycine ethyl ester, β-phenylalanine propyl ester or β-phenylalanine methyl ester; and amine derivatives of carbohydrates, such as glucosamine.

Where the amino acids and amines mentioned above can exist in the form of stereoisomers or optical isomers, it is possible to use any of the isomers or mixtures thereof.

Preferred amines are t-octylamine, benzylamine, dibenzylamine, N,N-dimethylbenzylamine, cyclohexylamine, dicyclohexylamine, N,N-dimethylcyclohexylamine, N-methylpyrrolidine, morpholine, L-leucine alkyl esters, dialkyl L-glutamates, D-phenylglycine alkyl esters and D-glucosamine; of which the most preferred amines are t-octylamine, dibenzylamine, dicyclohexylamine, morpholine, D-phenylglycine alkyl esters and D-glucosamine.

Esters of 6-methoxy-IsoML-236B-carboxylic acid may be represented by formula (V):

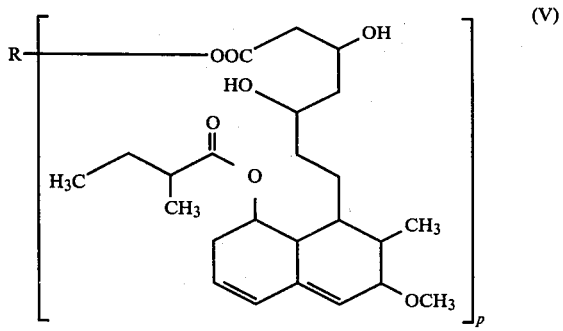

(V)

(in which R represents the alcoholic moiety of an ester and p represents the valency of R).

Where p represents 1, R preferably represents an alkyl group, an unsubstituted benzyl group, a substituted benzyl group having at least one substituent selected from alkyl groups, alkoxy groups and halogen atoms, an unsubstituted phenacyl group or a substituted phenacyl group having at least one substituent selected from alkyl groups, alkoxy groups and halogen atoms.

Where R represents an alkyl group, this may be a straight or branched chain group and preferably has from 1 to 6 carbon atoms. Examples of such a group include the methyl, ethyl, propyl, isopropyl, butyl, pentyl and hexyl groups.

Where R represents a benzyl group, this may be unsubstituted or substituted, the substituents preferably being $C_1$ or $C_2$ alkyl or alkoxy groups or halogen atoms. One or more, preferably one, substituents are possible and, if there is more than one substituent, these may be the same or different. Examples of such benzyl groups include the benzyl, 2-methylbenzyl, 3-methylbenzyl, 4-methylbenzyl, 2-ethylbenzyl, 3-ethylbenzyl, 4-ethylbenzyl, 2-methoxybenzyl, 3-methoxybenzyl, 4-methoxybenzyl, 2-ethoxybenzyl, 3-ethoxybenzyl, 4-ethoxybenzyl, 2-chlorobenzyl, 3-chlorobenzyl, 4-chlorobenzyl, 2-bromobenzyl, 3-bromobenzyl and 4-bromobenzyl groups.

R may represent an unsubstituted or substituted phenacyl group, in which the substituents are preferably $C_1$ or $C_2$ alkyl or alkoxy groups or halogen atoms. One or more, preferably one, substituents are possible and, where there is more than one substituent, these may be the same or different. Examples of such phenacyl groups include the phenacyl, 2-methylphenacyl, 3-methylphenacyl, 4-methylphenacyl, 2-ethylphenacyl, 3-ethylphenacyl, 4-ethylphenacyl, 2-methoxyphenacyl, 3-methoxyphenacyl, 4-methoxyphenacyl, 2-ethoxyphenacyl, 3-ethoxyphenacyl, 4-ethoxyphenacyl, 2-chlorophenacyl, 3-chlorophenacyl, 4-chlorophenacyl, 2-bromophenacyl, 3-bromophenacyl and 4-bromophenacyl groups.

Where p is 2, R represents a bivalent alcoholic moiety, preferably a $C_2$–$C_6$ alkylene or alkylidene group, for example, an ethylene, ethylidene, propylene, propylidene, trimethylene, tetramethylene, butylidene, pentamethylene or pentylidene group, as well as such groups having one or more substituents, e.g. hydroxy groups, halogen atoms, or trifluoromethyl groups.

Where p is 3, R represents a trivalent alcoholic moiety and it is preferably a saturated aliphatic hydrocarbon group having from 2 to 6 carbon atoms and optionally one or more substituents, e.g. hydroxy groups, halogen atoms or trifluoromethyl groups.

We prefer that p should be 1 and that R should represent an alkyl group (most preferably methyl, ethyl, propyl, isopropyl, butyl, isobutyl or hexyl), an optionally substituted benzyl group (most preferably benzyl, 4-methylbenzyl, 4-methoxybenzyl or 4-chlorobenzyl) or an optionally substituted phenacyl group (most preferably phenacyl, 4-methylphenacyl, 4-methoxyphenacyl or 4-bromophenacyl).

The most preferred groups represented by R are the methyl, ethyl, propyl, isopropyl, butyl and isobutyl groups.

The compounds of the invention have been found to inhibit cholesterol biosynthesis in the liver and thus may be used for the treatment of hypercholesteraemia or the prevention of arteriosclerosis, in the same way as are the compounds disclosed in U.S. Patent Application Ser. No. 256,243, filed Apr. 21, 1981, or U.S. Patent Application Ser. No. 270,846, filed June 5, 1981.

The inhibitory activities of certain of the compounds of the invention, in terms of the concentration in μg/ml required to inhibit cholesterol biosynthesis by 50% [measured by the method described in the Journal of Biological Chemistry, 234, 2835 (1959)], are as follows:

| | |
|---|---|
| 6-methoxy-IsoML-236B lactone | 0.015 |
| Sodium 6-methoxy-IsoML-236B carboxylate | 0.0044 |

For comparison, the value for ML-236B lactone is 0.010 μg/ml, which is comparable with the levels achieved by the compounds of the invention, but, as previously noted, by virtue of their resistance to in vivo degradation, the activity of the compounds of the invention is far more persistent.

The compounds of the invention may be administered by any conventional means, for example parenterally (e.g. by subcutaneous, intravenous or intramuscular injection) or orally (e.g. in the form of tablets, capsules, powders or granules). The adult daily dose will, of course, vary depending upon the age, body weight and condition of the patient, as well as upon the route and times of administration, but, in general, the compounds of the invention are preferably administered in an amount of from 0.5 to 500 mg/day, for adults, in a single dose or in divided doses, preferably 3 or 4 times per day.

The enzymatic alkoxylation process of the present invention is preferably effected by contacting ML-236B lactone, ML-236B carboxylic acid or a salt or ester of said acid (hereinafter collectively referred to as the "ML-236B compound") with a microorganism of the genus Syncephalastrum, Absidia or Cunninghamella which is capable of converting the ML-236B compound to the desired compound of the invention or contacting said ML-236B compound with an enzyme-containing extract from said microorganism, and then separating the compound of the invention from the culture medium or the reaction mixture.

Any microorganism capable of converting the ML-236B compound to the compound of formula (I) or (II) or salt or ester thereof may be employed, although microorganisms of the genera Syncephalastrum, Absidia or Cunninghamella, all of which are members of the Zygomycetes, are preferred. Particularly preferred are *Syncephalastrum racemosum* IFO-4814, *Syncephalastrum racemosum* IFO-4828, *Absidia coerulea* IFO-4423 and *Cunninghamella echinulata* IFO-4445. These microorganisms are all available, under the accession numbers given, from the Institute for Fermentation, Osaka, Japan.

Conversion of the ML-236B compound to the compound of the invention may be achieved by contacting the complete cellular microorganism or, in some cases, a cell-free extract from the microorganism with the ML-236B compound. The form of the compound produced will depend upon the culture conditions and the form of the microorganism employed. Thus, for example, if the complete cellular microorganism is cultivated in the presence of the ML-236B compound, the product may be the carboxylic acid, the lactone, the ester (especially alkyl ester) or the salt (especially alkali metal salt), depending upon the culture conditions, particularly the pH value. On the other hand, if the ML-236B compound is simply contacted with a resting cellular system or with a cell-free extract, the compound of the invention is most frequently obtained in the form of the alkali metal salt.

The progress of the conversion reaction may be determined by assaying samples of the reaction mixture during the course of the reaction to determine the degree of conversion.

Where the microorganisms are to be cultivated in the presence of the ML-236B compound to produce the compounds of the invention, the culture conditions and culture media employed will be chosen having regard to the particular microorganism to be cultivated. Since the species of microorganism proposed for use in the process of the present invention are well known, culture conditions and culture media for use with these microorganisms are also well known.

The compounds of the invention may be separated from the reaction mixture by conventional means, for example by filtering off microbial cells (if necessary) and then subjecting the remaining mixture to any combination of thin layer chromatography, column chromatography or high performance liquid chromatography. The various compounds of the invention, or various isomers of the compounds of the invention, where two or more are prepared together, may, if desired, be separated from each other in the course of one or more of these chromatographic purification steps or they may be separated as a mixture.

Where the enzymatic alkoxylation process of the invention produces 6-methoxy-IsoML-236B carboxylic acid or 6-methoxy-IsoML-236B lactone, these may be converted by conventional chemical reactions to the corresponding salts or esters (in the case of the carboxylic acid, if desired, this may first be converted to the lactone). For example, metal salts [that is to say compounds of formula (III)] and amino acid salts [that is to say compounds of formula (IV) in which A represents an amino acid] may be prepared by the method described in United Kingdom Patent Specification No. 1,555,831 for the preparation of salts of ML-236B carboxylic acid.

Amine salts may be prepared by reacting an alkali metal 6-methoxy-IsoML-236B carboxylate (for example the sodium carboxylate) with a mineral acid (e.g. hydrochloric acid) salt of ammonia or of an organic amine in a suitable solvent. The nature of the solvent is not critical, provided that it has no adverse effect upon the reaction, aqueous solvents being preferred. Examples of such solvents include water itself and mixtures of water with one or more organic solvents, such as alcohols (e.g. methanol or ethanol) or ketones (e.g. acetone). The amount of amine salt is preferably equimolar or a slight molar excess, with respect to the metal carboxylate, e.g. a molar ratio amine salt:metal carboxylate of from 1:1 to 1.2:1. The reaction is preferably effected at a pH value of from 7.0 to 8.5 and at a temperature of ambient or below, e.g. from 0° C. to 10° C., more preferably from 5° C. to 10° C. After the reaction, the resulting salt may be separated from the reaction mixture by extraction with a suitable solvent, such as ethyl acetate.

Esters of 6-methoxy-ML-236B carboxylic acid [that is to say compounds of formula (V)] may be prepared by esterification of the 6-methoxy-IsoML-236B lactone or carboxylic acid, as described in United Kingdom Patent Specification No. 1,555,831 in relation to the preparation of esters of ML-236B carboxylic acid, i.e. either by reaction of the 6-methoxy-IsoML-236B compound with an alcohol in the presence of a suitable catalyst or by reaction of this compound with a diazo compound, preferably diazomethane or a C-substituted diazomethane.

The invention is further illustrated by the following Examples.

EXAMPLE 1

Preparation of 6-methoxy-IsoML-236B lactone

Twenty 500 ml Erlenmeyer flasks, each containing 100 ml of a medium having the composition described below, were inoculated with spores of *Absidia coerulea* IFO-4423. The flasks were subjected to shaking culture at 26° C. and 220 strokes per minute (s.p.m) for 4 days. At the end of this time, ML-236B lactone was then added to each of the flasks to a final concentration of 0.05% w/v. Cultivation was continued at 26° C. and 220 s.p.m. for a further 6 days.

The composition of the medium was (percentages are w/v:):

| | |
|---|---|
| Glucose | 2.0% |
| $K_2HPO_4$ | 0.15% |
| $MgSO_4.7H_2O$ | 0.15% |
| $NH_4NO_3$ | 0.1% |
| Peptone | 0.1% |
| Corn Steep Liquor | 0.2% |
| Yeast extract | 0.1% |
| $ZnSO_4.7H_2O$ | 0.001% |
| Tap water | the balance |
| | (Adjusted to pH 7.0) |

After completion of the cultivation, the reaction liquor was filtered, and the filtrate was adjusted with trifluoroacetic acid to pH 3. The resulting mixture was extracted with three 1 liter portions of ethyl acetate, to give extracts containing 6-methoxy-IsoML-236B carboxylic acid.

The extracts were combined and were then washed with a saturated aqueous solution of sodium chloride and dried over anhydrous sodium sulfate, after which a catalytic amount of trifluoroacetic acid was added for lactonization. The resulting mixture was then washed with a 5% w/v aqueous solution of sodium bicarbonate, dried over anhydrous sodium sulfate and evaporated to dryness under reduced pressure. The residue was purified by chromatography through a Lobar column (Merck Si 60, size A) eluted with a 7:3 by volume mixture of benzene and acetone, to give 23 mg of 6-methoxy-IsoML-236B lactone.

6-Methoxy-IsoML-236B lactone has the following physical properties:

1. The Nuclear Magnetic Resonance spectrum, measured at 90 MHz in deuterochloroform using tetramethylsilane as the internal standard, was as follows, δ ppm:
   6.15 (1H, doublet);
   5.70 (1H, quartet);
   5.70 (1H, multiplet);
   5.40 (1H, multiplet);
   4.60 (1H, multiplet);
   4.40 (1H, multiplet);
   3.45 (1H, doublet);
   3.30 (3H, singlet).
2. Ultraviolet Absorption spectrum (methanol)-$\lambda_{max}$nm: 235.
3. Infrared Absorption spectrum (thin film)$\nu_{max}$cm$^{-1}$: 3450, 1730.
4. Mass spectrum
   m/e: 420 (M$^+$), 402, 318, 300, 286, 268.
5. Thin layer chromatography
   Plate: Merck silica gel Art 5715:
   Solvent: benzene/acetone (1:1 by volume): Rf value: 0.7
6. Elemental analysis:
   Calculated for $C_{24}H_{36}O_6$: C, 68.54%; H, 8.63%. Found: C, 68.53%; H, 8.81%.

EXAMPLE 2

Preparation of sodium 6-methoxy-IsoML-236B carboxylate 1 g of 6-methoxy-IsoML-236B lactone was dissolved in a small amount of acetone, and 13 ml of a 0.2 N aqueous solution of sodium hydroxide were added to the resulting solution. The mixture was allowed to stand at 40° C. for 1 hour to allow the hydrolysis to take place. After completion of the reaction, the acetone was distilled from the reaction mixture and the resulting residue was washed with 5 ml of chloroform. The aqueous phase was adjusted to a pH value of 8.0 by the addition of 0.1 N hydrochloric acid. The fraction containing the desired sodium 6-methoxy-IsoML-236B carboxylate was adsorbed on a Diaion HP-20 column (a product of Mitsubishi Chemical Industries Co.). The fraction containing the sodium 6-methoxy-IsoML-236B carboxylate was then eluted with 50% v/v aqueous acetone. The acetone was distilled from the eluate and the residue was freeze-dried, to give 1.003 g of the desired sodium 6-methoxy-IsoML-236B carboxylate.

Sodium 6-methoxy-IsoML-236B carboxylate has the following physical properties:
1. The Nuclear Magnetic Resonance spectrum, measured at 60 MHz in deuteromethanol using tetramethylsilane as the internal standard, was as follows, δ ppm:
   3.31 (3H, singlet);
   5.42 (1H, multiplet);
   5.70 (1H, multiplet);
   5.71 (1H, quartet);
   6.12 (1H, doublet).
2. Ultraviolet Absorption spectrum (methanol)-$\lambda_{max}$nm: 235.
3. Infrared Absorption spectrum (thin film)$\nu$cm$^{-1}$: 3400, 2950, 1580.
4. Elemental analysis: Calculated for $C_{24}H_{37}O_7Na$: C, 62.61%; H, 8.04%. Found: C, 62.54%; H, 8.11%.

EXAMPLE 3

Preparation of methyl 6-methoxy-IsoML-236B carboxylate 1 g of sodium 6-methoxy-IsoML-236B carboxylate was dissolved in a small amount of methanol, and then the resulting solution was acidified by the addition of trifluoroacetic acid, with cooling. A stoichiometric excess of an ethereal solution of diazomethane was immediately added and the mixture was allowed to stand for 30 minutes. At the end of this time, the solvent was distilled off and the resulting residue was purified through a Lobar column (Merck RP-8, size B), eluted with a 6:4 by volume mixture of methanol and water, to give 780 mg of the desired methyl 6-methoxy-IsoML-236B carboxylate, as a colourless oil having the following physical properties:

1. The Nuclear Magnetic Resonance spectrum, measured at 60 MHz in deuterochloroform using tetramethylsilane as the internal standard, was as follows, δ ppm:
   3.30 (3H, singlet);
   3.60 (3H, singlet);
   4.37 (1H, multiplet);
   4.62 (1H, multiplet);
   5.30 (1H, multiplet);
   5.70 (1H, multiplet);
   5.71 (1H, quartet);
   6.13 (1H, doublet).
2. Ultraviolet Absorption spectrum (methanol)-$\lambda_{max}$nm. 235.
3. Infrared Absorption spectrum (thin film)$\nu_{max}$cm$^{-1}$: 3400, 1725.
4. Mass Spectrum:
   The instrument used was type D-300, manufactured by Nippon Electronics, and measurement was made after the compound had been silylated with N,O-bis(trimethylsilyl)trifluoroacetamide, m/e: 668 (M$^+$)
5. Elemental analysis:
   Calculated for $C_{25}H_{40}O_7$: C, 66.34%; H, 8.91%. Found: C, 66.38%; H, 8.98%.

EXAMPLE 4

Preparation of 6-methoxy-IsoML-236B lactone

Twenty 500 ml Erlenmeyer flasks, each containing 100 ml of a medium having the composition described below, were inoculated with spores of *Absidia coerulea* IFO-4423. The flasks were then subjected to shaking culture at 220 s.p.m. and 26° C. for 4 days. At the end of this time, methyl ML-236B carboxylate was added to each of the flasks to a final concentration of 0.05% w/v. Cultivation was continued at 220 s.p.m. and 26° C. for a further 6 days.

The composition of the medium was (percentages are w/v):

| | |
|---|---|
| Glucose | 2.0% |
| K$_2$HPO$_4$ | 0.15% |
| MgSO$_4$.7H$_2$O | 0.15% |
| NH$_4$NO$_3$ | 0.1% |
| Peptone | 0.1% |
| Corn Steep Liquor | 0.2% |
| Yeast extract | 0.1% |
| ZnSO$_4$.7H$_2$O | 0.001% |
| Tap water | the balance (Adjusted to pH 7.0) |

After completion of the cultivation, the reaction liquor was treated as described in Example 1, to give 11 mg of 6-methoxy-IsoML-236B lactone, having the same physical properties as did the product obtained in Example 1.

EXAMPLE 5

Preparation of 6-methoxy-IsoML-236B lactone

The procedure described in Example 1 was repeated, except that spores of *Syncephalastrum racemosum* IFO-4814 were used in place of the *Absidia coerulea* IFO-4423. 5 mg of the desired 6-methoxy-IsoML-236B lactone were obtained.

EXAMPLE 6

Preparation of 6-methoxy-IsoML-236B lactone

The procedure described in Example 1 was repeated, except that spores of *Cunninghamella echinulata* IFO-4445 were used in place of the *Absidia coerulea* IFO-4423. 3 mg of the desired 6-methoxy-IsoML-236B lactone were obtained.

EXAMPLE 7

Preparation of 6-methoxy-IsoML-236B lactone

Twenty 500 ml Erlenmeyer flasks, each containing 100 ml of a medium having the composition set forth in Example 1 were inoculated with spores of *Absidia coerulea* IFO-4423. The flasks were then subjected to shaking culture at 26° C. and 220 s.p.m. for 4 days. The resulting cluster of microorganisms was collected by centrifugation, washed with physiological saline and again collected by centrifugation. It was then suspended in 1.8 liters of a 0.1 M phosphate buffer solution (pH 7.0). Sodium ML-236B carboxylate and glucose were then added to the suspension to a final concentration of 0.05% and 0.2%, respectively. The culture was then maintained at 26° C., with shaking at 220 s.p.m., for a further 5 days. After this time, the reaction liquor was filtered and then treated as described in Example 1, affording 8 mg of 6-methoxy-IsoML-236B lactone.

We claim:

1. The compound having the following formula (I):

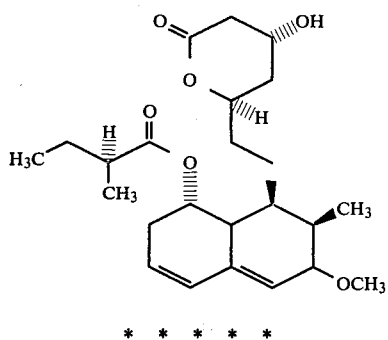

* * * * *